(12) United States Patent
Przewosny et al.

(10) Patent No.: US 6,716,872 B2
(45) Date of Patent: Apr. 6, 2004

(54) SUBSTITUTED PYRROLIDINE-2,3,4-TRIONE 3-OXIME DERIVATIVES WHICH ARE ACTIVE AS NMDA RECEPTOR ANTAGONISTS

(75) Inventors: Michael Przewosny, Aachen (DE); Hans-Dietrich Stachel, Neuried (DE); Hermann Poschen-Rieder, Graefelfing (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 10/066,801

(22) Filed: Feb. 6, 2002

(65) Prior Publication Data
US 2003/0027852 A1 Feb. 6, 2003

Related U.S. Application Data

(63) Continuation of application No. PCT/EP00/07101, filed on Jul. 25, 2000.

(30) Foreign Application Priority Data
Aug. 6, 1999 (DE) .......................... 199 36 521

(51) Int. Cl.$^7$ .................. A61K 31/40; C07C 207/40
(52) U.S. Cl. .................. 514/425; 548/546; 548/547
(58) Field of Search .................. 548/544, 545, 548/546, 547; 514/425

(56) References Cited

U.S. PATENT DOCUMENTS 2,832,790 A * 4/1958 Howard et al. .......... 260/326.3
5,554,768 A * 9/1996 Donges et al. .............. 548/545

* cited by examiner

Primary Examiner—Alan L. Rotman
Assistant Examiner—Ebenezer Sackey
(74) Attorney, Agent, or Firm—Crowell & Moring LLP

(57) ABSTRACT

Novel substituted pyrrolidine-2,3,4-trione compounds of formula I

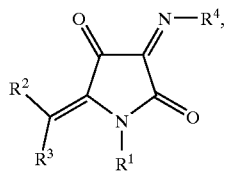

and methods for preparing the compounds. Also disclosed are pharmarceutical compositions comprising the compounds and methods of using the compounds for treating pain, anxiety and various other diseases or conditions.

29 Claims, No Drawings

SUBSTITUTED PYRROLIDINE-2,3,4-TRIONE 3-OXIME DERIVATIVES WHICH ARE ACTIVE AS NMDA RECEPTOR ANTAGONISTS

CROSS REFERENCE TO RELATED APPLICATIONS

The present application is a continuation of international patent application No. PCT/EP00/07101, filed Jul. 25, 2000, designating the United States of America, the entire disclosure of which is incorporated herein by reference. Priority is claimed based on Federal Republic of Germany patent application no. DE 199 36 521.0, filed Aug. 6, 1999.

BACKGROUND AND SUMMARY OF THE INVENTION

The invention relates to substituted pyrrolidine-2,3,4-trione 3-oxime derivatives, processes for their preparation, pharmaceutical compositions comprising these compounds, and methods for using these compounds for the preparation of pharmaceutical compositions and for the treatment of various diseases or conditions.

The treatment of chronic and non-chronic states of pain is of great importance in medicine. There is a worldwide demand for pain treatments which have a good efficacy. The urgent need for action in respect of patient-relevant and target-orientated treatment of chronic and non-chronic states of pain, this being understood as meaning successful and satisfactory pain treatment for the patient, is documented in the large number of scientific works which have recently appeared in the field of applied analgesia and fundamental research on nociception.

Conventional opioids, such as morphine, have a good action in the treatment of severe to very severe pain. However, their use is limited due to the known side effects, e.g. respiratory depression, vomiting, sedation, constipation, addiction, dependency and development of tolerance. They can therefore be administered over a relatively long period of time or in relatively high dosages only with particular safety precautions, such as specific prescription instructions (Goodman, Gilman, The Pharmacological Basis of Therapeutics, Pergamon Press, New York 1990). Furthermore, they have a relatively low efficacy for some states of pain, in particular neuropathic and incidental pain.

Opioids display their analgesic action by binding to receptors on the membrane which belong to the family of so-called G protein-coupled receptors. In addition, there are further receptors and ion channels which are considerably involved in the system of pain formation and pain conduction, such as the N-methyl-D-aspartate (NMDA) ion channel, via which a considerable part of the communication of synapses proceeds and through which the calcium ion exchange between a neuronal cell and its environment is controlled.

Knowledge of the physiological importance of ion channel-selective substances has been acquired by the development of the patch clamp technique, with which the action of NMDA antagonists on the calcium balance inside the cell can be demonstrated.

An object on which the invention is based was to provide new compounds which are suitable for pain treatment or for anxiolysis. Furthermore, these compounds should have as few as possible of the side effects of opioid analgesics, e.g. nausea, vomiting, dependency, respiratory depression or constipation. Further objects were to provide new active compounds for treatment of inflammatory and/or allergic reactions, depressions, drug and/or alcohol abuse, gastritis, diarrhoea, urinary incontinence, cardiovascular diseases, respiratory tract diseases, coughing, mental illnesses, epilepsy, schizophrenia, Alzheimer's disease, Huntington's disease, Parkinson's disease, cerebral ischaemias, cerebral infarctions, psychoses caused by increased amino acid levels, apoplexies, cerebral oedemas, hypoxia, anoxia, AIDS dementia, encephalomyelitis, Tourette's syndrome or perinatal asphyxia.

DETAILED DESCRIPTION OF THE INVENTION

It has now been found that substituted pyrrolidine-2,3,4-trione 3-oxime derivatives of the following general formula I, as NMDA antagonists, selectively attack the glycine binding site and are suitable for treatment of inflammatory and/or allergic reactions, depressions, drug and/or alcohol abuse, gastritis, diarrhoea, urinary incontinence, cardiovascular diseases, respiratory tract diseases, coughing, mental illnesses, epilepsy, schizophrenia, Alzheimer's disease, Huntington's disease, Parkinson's disease, cerebral ischaemias, cerebral infarctions, psychoses caused by increased amino acid levels, apoplexies, cerebral oedemas, hypoxia, anoxia, AIDS dementia, encephalomyelitis, Tourette's syndrome or perinatal asphyxia, and which moreover have a pronounced analgesic or anxiolytic action.

The present invention therefore provides compounds of the general formula I

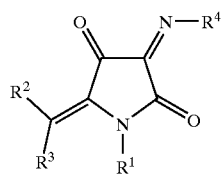

wherein the radical $R^1$ represents H, $OR^8$, $COR^5$, $CSR^5$, $NR^6R^7$, $COOR^5$, $CONR^6R^7$, $CSNR^6R^7$, a $C_{1-10}$-alkyl, preferably a $C_{1-6}$-alkyl, an aryl or a heteroaryl radical or represents an aryl radical bonded via a $C_{1-6}$-alkylene group, preferably an aryl radical bonded via a $C_{1-3}$-alkylene group, the radicals $R^2$, $R^3$, which are identical or different, represent H, F, Cl, Br, $CF_3$, $OR^8$, $SR^8$, a $C_{1-10}$-alkyl, preferably a $C_{1-6}$-alkyl, an aryl or a heteroaryl radical or represent an aryl radical bonded via a $C_{1-6}$-alkylene group, preferably an aryl radical bonded via a $C_{1-3}$-alkylene group, the radical $R^4$ represents H, OH, $OR^8$, $SR^8$, $COR^5$, $COOR^5$, $COCOR^5$, $CONR^6R^7$, $CSNR^6R^7$, preferably OH or $OR^8$, a $C_{1-10}$-alkyl, preferably a $C_{1-6}$-alkyl, an aryl or a heteroaryl radical or represents an aryl radical bonded via a $C_{1-6}$-alkylene group, preferably an aryl radical bonded via a $C_{1-3}$-alkylene group, the radical $R^5$ represents H, a $C_{1-10}$-alkyl, preferably a $C_{1-6}$-alkyl, an aryl or a heteroaryl radical or represents an aryl radical bonded via a $C_{1-6}$-alkylene group, preferably an aryl radical bonded via a $C_{1-3}$-alkylene group, the radicals $R^6$, $R^7$, which are identical or different, represent H, $OR^8$, $COR^5$, $COOR^5$, a $C_{1-10}$-alkyl, preferably a $C_{1-6}$-alkyl, an aryl or a heteroaryl radical or represent an aryl radical bonded via a $C_{1-6}$-alkylene group, preferably an aryl radical bonded via a $C_{1-3}$-alkylene group, the radical $R^8$ represents a $C_{1-10}$-alkyl, preferably a $C_{1-6}$-alkyl, an aryl or a heteroaryl radical or represents an aryl radical bonded via a $C_{1-6}$-alkylene group, preferably an aryl radical bonded via a $C_{1-3}$-alkylene group, in the form of their racemates, enantiomers, diastereomers or a corresponding base or a corresponding physiologically tolerated salt.

Alkyl radicals are also understood as meaning branched, unbranched or cyclic hydrocarbons which are unsubstituted or at least monosubstituted, preferably by F, Cl, Br, CN, $NO_2$, CHO, $SO_2C_{1-6}$-alkyl, $SO_2CF_3$, $OR^5$, $NR^6R^7$, $COR^5$, $COOR^5$, $COCOR^5$, $CONR^6R^7$ or $CSNR^6R^7$, where the radicals $R^5$ to $R^7$ have the meaning according to the general formula I. If these alkyl radicals contain more than one substituent, these can be identical or different. The alkyl radicals are preferably methyl, ethyl, propyl, isopropyl, n-butyl, sec-butyl, tert-butyl, neopentyl, n-hexyl, cyclopropyl, cyclobutyl, cyclopentyl or cyclohexyl.

An aryl radical is also understood as meaning phenyl radicals which are unsubstituted or at least monosubstituted by OH, F, Cl, Br, $CF_3$, CN, $NO_2$, CHO, $SO_2C_{1-6}$-alkyl, $SO_2CF_3$, $OR^5$, $NR^6R^7$, $COR^5$, $COOR^5$, $COCOR^5$, $CONR^6R^7$, $CSNR^6R^7$, a $C_{1-6}$-alkyl radical, a $C_{1-6}$-alkoxy radical, a $C_{2-6}$-alkylene radical, a heterocyclyl radical and/or a phenyl radical, wherein the radicals $R^5$ to $R^7$ have the meaning according to the general formula I. The term can also denote an optionally substituted naphthyl radical. The phenyl radicals can also be fused with further rings.

A heteroaryl radical is also understood as meaning 5- or 6-membered unsaturated heterocyclic compounds which are optionally provided with a fused-on aryl radical and contain at least one heteroatom, preferably nitrogen and/or oxygen and/or sulfur.

The heteroaryl radical is preferably furan, thiophene, pyrrole, pyridine, pyrimidine, quinoline, isoquinoline, phthalazine or quinazoline.

The following substituted pyrrolidine-2,3,4-trione 3-oxime derivatives are particularly preferred:

5-(methoxyphenylmethylene)-pyrrolidine-2,3,4-trione 3-oxime 5-(bromophenylmethylene)-pyrrolidine-2,3,4-trione 3-oxime 5-benzylidene-pyrrolidine-2,3,4-trione 3-oxime, 5-(2-chlorobenzylidene)-pyrrolidine-2,3,4-trione 3-oxime 5-(4-chlorobenzylidene)-pyrrolidine-2,3,4-trione 3-oxime 5-(2,3-dichlorobenzylidene)-pyrrolidine-2,3,4-trione 3-oxime 5-(2,4-dichlorobenzylidene)-pyrrolidine-2,3,4-trione 3-oxime 5-(2,6-dichlorobenzylidene)-pyrrolidine-2,3,4-trione 3-oxime and 5-(3-chlorobenzylidene)-pyrrolidine-2,3,4-trione 3-oxime.

The present invention also provides processes for the preparation of substituted pyrrolidine-2,3,4-trione 3-oxime derivatives of the general formula I, in which tetramic acids of the general formula II

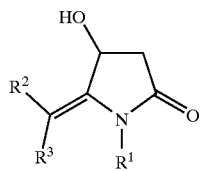

II wherein the radicals $R^1$ to $R^3$ have the meaning according to the general formula I, are reacted with an aqueous solution of sodium nitrite in an ice-cooled solution, preferably in an ice-cooled solution of glacial acetic acid, to give compounds of the general formula I wherein the radical $R^4$ represents OH and the radicals $R^1$ to $R^3$ have the meaning according to the general formula I, and these are preferably purified by recrystallization, preferably from ethanol, and isolated.

The synthesis of the starting compounds, the tetramic acids of the general formula II, can be carried out in accordance with H. Poschenrieder et al. (Arch. Pharm. Pharm. Med. Chem. 1998, vol. 331, pages 389–394) and Stachel et al. (J. Heterocycl. Chem. 1980, vol. 17, pages 1195–1199 and Liebigs Ann. Chem. 1985, pages 1692–1696) and the literature references cited therein. They are included herewith as reference and are therefore part of the disclosure.

The compounds of the general formula I wherein the radical $R^4$ represents OH and the radicals $R^1$ to $R^3$ have the meaning according to the general formula I are reacted with $C_{1-10}$-alkyl halides, preferably with $C_{1-6}$-alkyl halides, with aryl halides, heteroaryl halides or with aryl-$C_{1-6}$-alkyl halides, preferably with aryl-$C_{1-3}$-alkyl halides, preferably under an inert gas atmosphere in absolute solvents, preferably in open-chain and/or cyclic ethers, at low temperatures in the presence of strong bases, preferably alkali metal hydroxides and/or alkaline earth metal hydroxides and/or organometallic bases, to give compounds of the general formula I wherein the radical $R^4$ represents $OR^8$ and the radicals $R^1$ to $R^3$ and $R^8$ have the meaning according to the general formula I.

The compounds of the general formula I wherein the radical $R^4$ represents $OR^8$ and the radicals $R^1$ to $R^3$ and $R^8$ have the meaning according to the general formula I can be derivatized still further in that they are reacted with acid chlorides of the general formula $R^5$—(C=O)—Cl and/or acid bromides of the general formula $R^5$—(C=O)—Br or chloroformic acid esters of the general formula Cl—(C=O)—O—$R^5$ or fluoroformic acid esters of the general formula F—(C=O)—O—$R^5$ or with open-chain carbonates of the general formula $R^5$—O—(C=O)—O—$R^5$ or with correspondingly substituted cyclic carbonates, preferably with correspondingly substituted cyclic carbonates which contain 5 or 6 atoms in the ring, wherein in each case the radical $R^5$ has the meaning according to the general formula I, preferably under an inert gas atmosphere in an absolute solvent, preferably in open-chain and/or cyclic ethers, to give compounds of the general formula I wherein the radical $R^4$ represents $COR^5$ and $COOR^5$ and the radicals $R^1$ to $R^3$ and the radical $R^5$ have the meaning according to the general formula I, are purified and isolated by conventional processes.

The compounds of the general formula I wherein the radical $R^4$ represents OH and the radicals $R^1$ to $R^3$ have the meaning according to the general formula I can also be reacted with aliphatic, aromatic and heteroaromatic isocyanates or isothiocyanates at low temperatures in aprotic, polar solvents to give compounds of the general formula I wherein the radical $R^4$ represents $CONR^6R^7$ or $CSNR^6R^7$, the radical $R^6$ or $R^7$ denotes H and the radicals $R^1$ to $R^3$ and $R^6$ and $R^7$ have the meaning according to the general formula I, are purified and isolated by conventional processes.

The preparation of the compounds of the general formula I in which the radical $R^4$ represents a $C_{1-10}$-alkyl radical, an aryl radical or a heteroaryl radical or represents an aryl radical bonded via a $C_{1-6}$-alkylene group can be carried out by the method described in Maruoka and Yamamoto, Angew. Chem., vol. 97, pp. 670–683, 1985, Maruoka et al. J. Am. Chem. Soc., vol. 105, p. 2831, 1985 or Maruoka et al. Org. Synth., vol. 66, p. 185. The corresponding disclosures are included herewith as reference.

The preparation of the compounds of the general formula I wherein the radical $R^4$ represents H, $SR^8$ or $COCOR^5$ and the radicals $R^5$ and $R^8$ have the meaning according to the general formula I can be carried out by the various methods known to the expert. The preparation of the compounds of the general formula I wherein the radical $R^4$ represents $CONR^6R^7$ or $CSNR^6R^7$ and the radicals $R^6$ and $R^7$ either each denote H or each have the meaning of the general formula I but are not H can also be carried out by the various methods known to the expert.

Analyses by means of $^1$H-NMR spectroscopy show that the pyrrolidine-2,3,4-trione 3-oxime derivatives of the general formula I obtained by the abovementioned processes can be present as a mixture of syn and anti isomers, which it has not been possible to separate further.

The compounds of the general formula I according to the invention can be converted with acids, such as, for example, hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid, aspartic acid or a mixture of at least two of these acids into the corresponding physiologically tolerated salts in the manner known per se. The salt formation is preferably carried out in a solvent, such as, for example, diethyl ether, diisopropyl ether, acetic acid alkyl esters, acetone, 2-butanone or a mixture of at least two of these solvents. Trimethylchlorosilane in aqueous solution is moreover suitable for preparation of the corresponding hydrochlorides.

The substituted pyrrolidine-2,3,4-trione 3-oxime derivatives of the general formula I according to the invention are toxicologically acceptable and therefore represent suitable pharmaceutical active compounds.

The invention therefore also provides medicaments which comprise, as the active compound, at least one substituted pyrrolidine-2,3,4-trione 3-oxime derivative of the general formula I and/or a corresponding base and/or a corresponding physiologically tolerated salt, and optionally further active compounds and/or auxiliary substances. The medicament can also comprise a mixture of at least two enantiomers and/or the corresponding bases and/or the corresponding physiologically tolerated salts of a compound of the general formula I according to the invention, wherein the enantiomers are not present in equimolar amounts.

The medicaments are preferably employed for treatment or control of pain, inflammatory and/or allergic reactions, depressions, drug and/or alcohol abuse, gastritis, diarrhoea, urinary incontinence, cardiovascular diseases, respiratory tract diseases, coughing, mental illnesses, neurodegenerative diseases, epilepsy, schizophrenia, Alzheimer's disease, Huntington's disease, Parkinson's disease, cerebral ischaemias, cerebral infarctions, psychoses caused by increased amino acid levels, apoplexies, cerebral oedemas, deficiency states of the central nervous system, hypoxia, anoxia, AIDS dementia, encephalomyelitis, Tourette's syndrome, perinatal asphyxia or for anxiolysis.

The invention also provides the use of at least one substituted pyrrolidine-2,3,4-trione 3-oxime derivative of the general formula I and/or a corresponding base and/or a corresponding physiologically tolerated salt for the preparation of a medicament for treatment/control for/of pain, inflammatory and/or allergic reactions, depressions, drug and/or alcohol abuse, gastritis, diarrhoea, urinary incontinence, cardiovascular diseases, respiratory tract diseases, coughing, mental illnesses, neurodegenerative diseases, epilepsy, schizophrenia, Alzheimer's disease, Huntington's disease, Parkinson's disease, cerebral ischaemias, cerebral infarctions, psychoses caused by increased amino acid levels, apoplexies, cerebral oedemas, deficiency states of the central nervous system, hypoxia, anoxia, AIDS dementia, encephalomyelitis, Tourette's syndrome, perinatal asphyxia or for anxiolysis.

To prepare corresponding pharmaceutical formulations, in addition to at least one substituted pyrrolidine-2,3,4-trione 3-oxime derivative of the general formula I, conventional auxiliary substances, or excipients, such as carrier materials, fillers, solvents, diluents, dyestuffs or binders, are additionally employed. The choice of auxiliary substances and the amounts thereof to be employed depends on the mode of administration, such as oral, intravenous, intraperitoneal, intradermal, intramuscular, intranasal, buccal or local, for example on infections on the skin, the mucous membranes and on the eyes, and is known to the expert. Formulations in the form of tablets, coated tablets, capsules, granules, drops, juices and syrups and multiparticulate formulations, for example pellets or granules, which can optionally also be filled in capsules or pressed to tablets, are suitable, for example, for oral administration, and solutions, suspensions, easily reconstitutable dry formulations and sprays e.g. are suitable for parenteral, topical and inhalatory administration. Compounds of the general formula I according to the invention in a depot, in dissolved form or in a patch, optionally with the addition of agents which promote penetration of the skin, are suitable percutaneous administration formulations. Formulation forms which can be used orally or percutaneously can also release the compounds of the general formula I according to the invention in a retarded manner.

The amount of active compound to be administered to the patient varies according to the weight of the patient, the mode of administration, the indication and the severity of the illness. 2 to 500 mg/kg of body weight of the patient of at least one pyrrolidine-2,3,4-trione 3-oxime derivative of the general formula I are usually administered.

Pharmacological Studies
a) Studies of the Receptor Binding

Studies for determination of the affinity of the substituted pyrrolidine-2,3,4-trione 3-oxime derivatives of the general formula I according to the invention for the glycine binding site of the NMDA receptor channel were carried out on cerebral membrane homogenates (homogenate of the cortex and hippocampus area from the brain of male rats, Wistar strain, Charles River, WIGA GmbH, Sulzbach, Germany) by the method of Baron B. M. et al, J. Pharmacol. Exp. Ther., vol. 279, pp.62–68 (1996).

For this, the cortex and hippocampus were dissected free from freshly removed rat brains and homogenized in 5 mmol/l TRIS-acetate buffer, 0.32 mol/l sucrose pH 7.4 (10 ml/g fresh weight) with a Potter homogenizer (Braun/Melsungen, Germany, 10 plunger strokes at 500 revolutions per minute (rpm)), while cooling with ice, and the homogenate was then centrifuged for 10 minutes at 1,000 g and 4° C. The first supernatant was collected and the sediment was homogenized again with 5 mmol/l TRIS-acetate buffer, 0.32 mol/l sucrose pH 7.4 (5 ml/g original fresh weight of rat brain cortex and hippocampus) with the Potter homogenizer (10 plunger strokes at 500 rpm), while cooling with ice, and the homogenate was centrifuged for 10 minutes at 1,000 g and 4° C. The resulting supernatant was combined with the supernatant from the first centrifugation and the mixture was centrifuged at 17,000 g for 20 minutes at 4° C. The supernatant after this centrifugation was discarded, the membrane sediment was taken up in 5 mmol/l TRIS-acetate buffer pH 8.0 (20 ml/g original fresh weight) and the mixture was homogenized with 10 plunger strokes at 500 rpm.

The membrane homogenate was then incubated for 1 hour at 4° C. and centrifuged for 30 minutes at 50,000 g and 4° C. The supernatant was discarded and the centrifuge tube with the membrane sediment was closed with Parafilm and frozen at −20° C. for 24 hours. The membrane sediment was then thawed and taken up in ice-cold 5 mmol/l TRIS-acetate buffer, 0.1% saponin (weight/volume) pH 7.0 (10 ml/g original fresh weight) and homogenized with 10 plunger strokes at 500 rpm and the homogenate was then centrifuged for 20 minutes at 50,000 g and 4° C. The resulting supernatant was discarded and the sediment was taken up in a small volume of 5 mmol/l TRIS-acetate buffer pH 7.0 (approx. 2 ml/g original fresh weight) and the mixture was homogenized again with 10 plunger strokes at 500 rpm. After determination of the protein content, the membrane homogenate was brought to a protein concentration of 10 mg protein/ml with 5 mmol/l TRIS-acetate buffer pH 7.0 and frozen in aliquots until the analysis was carried out.

For the receptor binding test, aliquots were thawed, diluted 1:10 with 5 mmol/l TRIS-acetate buffer pH 7.0, homogenized with 10 plunger strokes at 500 rpm with the Potter homogenizer, while cooling with ice, and centrifuged for 60 minutes at 55,000 g at 4° C. The supernatant was decanted and the membrane sediment was brought to a protein concentration of 1 mg/ml with ice-cold 50 mmol/l TRIS-acetate buffer pH 7.0, and the mixture was homogenized again with 10 plunger strokes at 500 rpm and kept in suspension while stirring on a magnetic stirrer in an ice-bath. 100 µl portions of this membrane homogenate were employed per 1 ml batch in the receptor binding test (0.1 mg protein/ml in the final batch).

In the binding test, 50 mmol/l TRIS-acetate buffer pH 7.0 was employed as the buffer and 1 nmol/l ($^3$H)-MDL 105.519 (Baron B. M. et al, J. Pharmacol. Exp. Ther., vol. 279, pp. 62–68 (1996)) was employed as the radioactive ligand. The proportion of non-specific binding was determined in the presence of 1 mmol/l glycine.

In further batches, the compounds according to the invention were added in concentration series and the displacement of the radioactive ligand from its specific binding to the glycine binding site of the NMDA receptor channel was determined. The particular triplicate batches were incubated for 120 minutes at 4° C. and then harvested by means of filtration through glass fibre filter mats (type Whatman GF/B, Adi Hassel, Munich, Germany) for determination of the radioactive ligand bonded to the membrane homogenate. The radioactivity retained on the glass fibre filters was measured in a β-counter (Packard TRI-CARB Liquid Scintillation Analyzer 2000CA, Packard Instrument, Meriden, Conn. 06450, USA) after addition of scintillator (Ready Protein, Beckmann Coulter GmbH, Krefeld, Germany).

The affinity of the compounds according to the invention for the glycine binding site of the NMDA receptor channel was calculated as the $IC_{50}$ (concentration with 50% displacement of the radioactive ligand from its specific binding) by the law of mass action by means of non-linear regression and is stated as the Ki value after conversion (by the Cheng-Prussoff equation (Y. Cheng, W. H. Prusoff, 1973, Biochem. Pharmacol., vol. 22, pp. 3099–3108)).

b) NMDA/glycine-induced Ion Currents in Xenopus Oocytes Injected with RNA

The study for determination of function changes of the NMDA receptor channel by the compounds of the general formula I according to the invention was carried out on oocytes of the South African clawed toad *Xenopus laevis*. For this, neuronal NMDA receptor channels were formed in oocytes after injection of RNA from mouse brains, and ion currents induced by co-application of NMDA and glycine were measured.

Xenopus oocytes of stages V and VI (Dumont, J. N., J. Morphol. 136, pp. 153–180 (1972)) were microinjected with complete RNA from brain tissue of adult mice (100–130 ng/cell) and were kept for up to 10 days in culture medium (composition: 88.0 mmol/l NaCl, 1.0 mmol/l KCl, 1.5 mmol/l $CaCl_2$, 0.8 mmol/l $MgSO_4$, 2.4 mmol/l $NaHCO_3$, 5 mmol/l HEPES, 100 IU/ml penicillin, 100 µg/ml streptomycin, pH 7.4) at 20° C. Transmembrane ion currents were recorded with the aid of the conventional two-electrode voltage clamping technique at a holding potential of −70 mV (Bloms-Funke P. et al, (1996) Neurosci. Lett. 205, pp. 115–118 (1996)). The OTC interface and Cellworks software (npi, Federal Republic of Germany) were used for recording data and controlling the test apparatus. The compounds according to the invention were added to a nominally $Mg^{2+}$-free medium (composition: 89.0 mmol/l NaCl, 1.0 mmol/l KCl, 1.8 mmol/l $CaCl_2$, 2.4 mmol/l $NaHCO_3$, 5 mmol/l HEPES, pH 7.4) and applied to the system with the aid of a concentration clamp (npi, Federal Republic of Germany). To test substance effects mediated via the glycine B-binding site of the NMDA receptor channel, the glycine dose/effect curve with and without the particular compound according to the invention was plotted. For this, NMDA was co-applied cumulatively in a fixed concentration of 100 µmol/l with glycine in increasing concentrations (0–100 µmol/l). Thereafter, the experiment was repeated in the same manner with a fixed concentration of the compound according to the invention. The current amplitudes were standardized to those of the control response to co-application of NMDA (100 µmol/l) with glycine (10 µmol/l). The data were analysed with the Igor-Pro software (version 3.1, WaveMetrics, USA). All the results were stated as the mean from at least 3 experiments on different oocytes of at least two toads. The significance for non-paired measurement parameters is determined with the aid of the Mann-Whitney U test and that for paired measurement parameters by the Wilcoxon test (Sysstat, SPSS Inc., USA). The $EC_{50}$ values are calculated according to the following equation:

$$Y = Y_{min} + (Y_{max} - Y_{min})/(1 + (X/EC_{50})^{-p})$$

($Y_{min}$=minimum test value, $Y_{max}$=maximum test value, Y=relative current amplitude, X=concentration of the test substance, p=slope factor). With a right-hand shift of the glycine dose/effect curve, the $pA_2$ value of the compound according to the invention was determined graphically with the aid of a Schild regression. Concentration ratios were calculated with the aid of the $EC_{50}$ values, which were calculated independently for each dose/effect curve.

c) Formalin Test in Mice

The studies for determination of the antinociceptive action of the compounds according to the invention were carried out in the formalin test in male albino mice (NMRI, 25–35 g, Iffa Credo, Belgium).

In the formalin test, a distinction is made between the first (early) phase (0–15 min after formalin injection) and the second (late) phase (15–60 min after formalin injection) (D. Dubuisson et al, Pain, vol. 4, pp. 161–174 (1977)). The early phase represents a model for acute pain, as a direct reaction to the formalin injection, while the late phase is regarded as a model for persistent (chronic) pain (T. J. Coderre et al, Pain, vol. 52, pp. 259–285 (1993).

The compounds according to the invention were investigated in the second phase of the formalin test to obtain information on the actions of the compounds according to the invention on chronic/inflammatory pain.

By a single subcutaneous formalin injection (20 μl, 1% aqueous solution) into the dorsal side of the right hind paw of freely mobile test animals, a nociceptive reaction was induced, which manifests itself in significant licking and biting of the paw affected.

For the investigation period in the second (late) phase of the formalin test, the nociceptive behavior was recorded continuously by observing the animals. The pain properties were quantified by adding up the seconds in which the animals showed licking and biting of the paw affected in the investigation period. After injection of substances which have an antinociceptive action in the formalin test, the modes of behaviour described for the animals are reduced, and possibly even eliminated. In a manner corresponding to the experiments in which the animals had received an injection of the compounds according to the invention before the administration of formalin, the control animals were injected with the vehicle, i.e. solvent (e.g. 0.9% NaCl solution) before the administration of formalin. The behaviour of the rats after administration of the substance was compared with a control group (10 mice per substance dose).

On the basis of the quantification of the pain properties, the action of the substance in the formalin test was determined as a change from the control in per cent. The $ED_{50}$ calculations were made by means of regression analysis. The administration time before the formalin injection was chosen according to the mode of administration of the compounds according to the invention (intraperitoneal: 15 min, intravenous: 5 min).

d) Writhing Test in the Mouse

The study of the analgesic activity was also carried out in the phenylquinone-induced writhing in the mouse (modified by I. C. Hendershot et al, (1959) J. Pharmacol. Exp. Ther., vol. 125, pp. 237–240). Male NMRI mice weighing 25 to 30 g (Iffa, Credo, Belgium, were used for this. Groups of 10 animals per substance dose received 0.3 ml/mouse of a 0.02% aqueous solution of phenylquinone (phenylbenzoquinone, Sigma, Deisenhofen; preparation of the solution with the addition of 5% ethanol and storage in a water bath at 45° C.) administered intraperitoneally 10 minutes after intravenous administration of the particular compound. The animals were placed individually in observation cages. The number of pain-induced stretching movements (so-called writhing reactions=straightening of the body with stretching of the hind extremities) was counted by means of a push-button counter for 5 to 20 minutes after the administration of phenylquinone. Animals which received only physiological saline solution were also run as a control. All the substances were tested in the standard dosage of 10 mg/kg of body weight of the mouse. The percentage inhibition (% inhibition) of the writhing reaction by a substance was calculated according to the following equation:

$$\% \text{ inhibition} = 100 - \frac{\text{writhing reactions of the treated animals}}{\text{writhing reactions of the control animals}} * 100$$

For some of the compounds according to the invention the $ED_{50}$ values with the 95% confidence range of the writhing reaction were calculated by means of regression analysis (evaluation program from Martens EDV Service, Eckental) from the dose-dependent decrease in the writhing reactions compared with phenylquinone control groups investigated in parallel.

The following examples serve to illustrate the invention, but do not limit the general inventive idea.

EXAMPLES

The yields of the compounds prepared are not optimized. The melting points determined are uncorrected.

Example 1

5-(Methoxyphenylmethylene)-pyrrolidine-2,3,4-trione 3-oxime

An aqueous solution of 1.1 mmol (0.075 g) sodium nitrite was added dropwise to an ice-cooled solution of 2 mmol 4-hydroxy-5-(methoxyphenyl-methylene)-1,5-dihydropyrrol-2-one (prepared in accordance with H. Poschenrieder et al (Arch. Pharm. Pharm. Med. Chem. 1998, 331, 389–394) and H. -D. Stachel et al (J. Heterocycl. Chem. 1980, vol. 17, pp. 1195–1199 and Liebigs Ann. Chem. 1985, pp. 1692–1696)) in 5 ml glacial acetic acid, while stirring. The resulting solution was then stirred at room temperature for 30 minutes and concentrated in vacuo. The residue is purified by recrystallization from ethanol. The yield of 5-(methoxyphenylmethylene)-pyrrolidine-2,3,4-trione 3-oxime was 60%, with a melting point of 174° C.

Analysis of this compound by means of $^1$H-NMR spectroscopy gave the following signals:

(d6-DMSO, δ in ppm): 11.95 (s, 1 H); 10.74 (s, 0.66 H); 10.71 (s, 0.33 H); 7.46 (m, 5 H); 3.42 (s, 1 H); 3.41 (s, 2 H).

Example 2

5-(Bromophenylmethylene)-pyrrolidine-2,3,4-trione 3-oxime

An aqueous solution of 1.1 mmol (0.075 g) sodium nitrite was added dropwise to an ice-cooled solution of 2 mmol 5-(bromophenyl-methylene)-4-hydroxy-1,5-dihydropyrrol-2-one (prepared in accordance with H. Poschenrieder et al (Arch. Pharm. Pharm. Med. Chem. 1998, 331, 389–394) and H. -D. Stachel et al (J. Heterocycl. Chem. 1980, vol. 17, pp. 1195–1199 and Liebigs Ann. Chem. 1985, pp. 1692–1696)) in 5 ml glacial acetic acid, while stirring. The resulting solution was then stirred at room temperature for 30 minutes and concentrated in vacuo. The residue is purified by recrystallization from ethanol. The yield of 5-(bromophenylmethylene)-pyrrolidine-2,3,4-trione 3-oxime was 65%, with a melting point of 158° C.

Analysis of this compound by means of $^1$H-NMR spectroscopy gave the following signals:

(d6-DMSO, δ in ppm): 14.46 (s, 1 H); 11.06 (s, 0.70 H); 11.00 (s, 0.30 H); 7.40–7.26 (m, 5 H).

Example 3

5-Benzylidene-pyrrolidine-2,3,4-trione 3-oxime

An aqueous solution of 1.1 mmol (0.075 g) sodium nitrite was added dropwise to an ice-cooled solution of 2 mmol 5-benzylidene 4-hydroxy-1,5-dihydropyrrol-2-one (prepared in accordance with H. Poschenrieder et al (Arch. Pharm. Pharm. Med. Chem. 1998, 331, 389–394) and H.-D. Stachel et al (J. Heterocycl. Chem. 1980, vol. 17, pp. 1195–1199 and Liebigs Ann. Chem. 1985, pp. 1692–1696)) in 5 ml glacial acetic acid, while stirring. The resulting solution was then stirred at room temperature for 30 minutes and concentrated in vacuo. The residue is purified by recrystallization from ethanol. The yield of 5-benzylidene-pyrrolidine-2,3,4-trione 3-oxime was 65%, with a melting point of 205° C.

Analysis of this compound by means of $^1$H-NMR spectroscopy gave the following signals:

(d6-DMSO, δ in ppm): 14.66 (s, 1 H); 11.25 (s, 0.66 H); 11.18 (s, 0.33 H); 7.64–7.31 (m, 5 H); 6.42 (s, 0.33 H); 6.36 (s, 0.66 H).

Example 4

5-(2-Chlorobenzylidene)-pyrrolidine-2,3,4-trione 3-oxime

An aqueous solution of 1.1 mmol (0.075 g) sodium nitrite was added dropwise to an ice-cooled solution of 2 mmol 5-(2-chlorobenzylidene)-4-hydroxy-1,5-dihydropyrrol-2-one (prepared in accordance with H. Poschenrieder et al (Arch. Pharm. Pharm. Med. Chem. 1998, 331, 389–394) and H.-D. Stachel et al (J. Heterocycl. Chem. 1980, vol. 17, pp. 1195–1199 and Liebigs Ann. Chem. 1985, pp. 1692–1696)) in 5 ml glacial acetic acid, while stirring. The resulting solution was then stirred at room temperature for 30 minutes and concentrated in vacuo. The residue is purified by recrystallization from ethanol. The yield of 5-(2-chlorobenzylidene)-pyrrolidine-2,3,4-trione 3-oxime was 60%, with a melting point of 176° C.

Analysis of this compound by means of $^1$H-NMR spectroscopy gave the following signals:

(d6-DMSO, δ in ppm): 11.40 (s, 0.66 H); 11.34 (s, 0.33 H); 7.46–7.21 (m, 4 H); 6.52 (s, 0.33 H); 6.47 (s, 0.66 H).

Example 5

5-(4-Chlorobenzylidene)-pyrrolidine-2,3,4-trione 3-oxime

An aqueous solution of 1.1 mmol (0.075 g) sodium nitrite was added dropwise to an ice-cooled solution of 2 mmol 5-(4-chlorobenzylidene)-4-hydroxy-1,5-dihydropyrrol-2-one (prepared in accordance with H. Poschenrieder et al (Arch. Pharm. Pharm. Med. Chem. 1998, 331, 389–394) and H.-D. Stachel et al (J. Heterocycl. Chem. 1980, vol. 17, pp. 1195–1199 and Liebigs Ann. Chem. 1985, pp. 1692–1696)) in 5 ml glacial acetic acid, while stirring. The resulting solution was then stirred at room temperature for 30 minutes and concentrated in vacuo. The residue is purified by recrystallization from ethanol. The yield of 5-(4-chlorobenzylidene)-pyrrolidine-2,3,4-trione 3-oxime was 50%, with a melting point of 190° C.

Analysis of this compound by means of $^1$H-NMR spectroscopy gave the following signals:

(d6-DMSO, δ in ppm): 11.35 (s, 0.66 H); 11.28 (s, 0.33 H); 7.67–7.64 (m, 2 H); 7.45–7.35 (m, 2 H); 6.40 (s, 0.33 H); 6.35 (s, 0.66 H).

Example 6

5-(2,3-Dichlorobenzylidene)-pyrrolidine-2,3,4-trione 3-oxime

An aqueous solution of 1.1 mmol (0.075 g) sodium nitrite was added dropwise to an ice-cooled solution of 2 mmol 5-(2,3-dichlorobenzylidene)-4-hydroxy-1,5-dihydropyrrol-2-one (prepared in accordance with H. Poschenrieder et al (Arch. Pharm. Pharm. Med. Chem. 1998, 331, 389–394) and H.-D. Stachel et al (J. Heterocycl. Chem. 1980, vol. 17, pp. 1195–1199) and Liebigs Ann. Chem. 1985, pp. 1692–1696)) in 5 ml glacial acetic acid, while stirring. The resulting solution was then stirred at room temperature for 30 minutes and concentrated in vacuo. The residue is purified by recrystallization from ethanol. The yield of 5-(2,4-dichlorobenzylidene)-pyrrolidine-2,3,4-trione 3-oxime was 55%, with a melting point of 180° C.

Analysis of this compound by means of $^1$H-NMR spectroscopy gave the following signals:

(d6-DMSO, δ in ppm): 11.43 (s, 0.66 H); 11.37 (s, 0.33 H); 7.63–7.37 (m, 3 H); 6.50 (s, 0.33 H); 6.45 (s, 0.66 H).

Example 7

5-(2,4-Dichlorobenzylidene)-pyrrolidine-2,3,4-trione 3-oxime

An aqueous solution of 1.1 mmol (0.075 g) sodium nitrite was added dropwise to an ice-cooled solution of 2 mmol 5-(2,4-dichlorobenzylidene)-4-hydroxy-1,5-dihydropyrrol-2-one (prepared in accordance with H. Poschenrieder et al (Arch. Pharm. Pharm. Med. Chem. 1998, 331, 389–394) and H.-D. Stachel et al (J. Heterocycl. Chem. 1980, vol. 17, pp. 1195–1199 and Liebigs Ann. Chem. 1985, pp. 1692–1696)) in 5 ml glacial acetic acid, while stirring. The resulting solution was then stirred at room temperature for 30 minutes and concentrated in vacuo. The residue is purified by recrystallization from ethanol. The yield of 5-(2,4-dichlorobenzylidene)-pyrrolidine-2,3,4-trione 3-oxime was 55%, with a melting point of 180° C.

Analysis of this compound by means of $^1$H-NMR spectroscopy gave the following signals:

(d6-DMSO, δ in ppm): 11.38 (s, 0.66 H); 11.32 (s, 0.33 H); 7.68–7.65 (m, 2 H); 7.45–7.43 (m, 1 H); 6.42 (s, 0.33 H); 6.36 (s, 0.66 H).

Example 8

5-(2,6-Dichlorobenzylidene)-pyrrolidine-2,3,4-trione 3-oxime

An aqueous solution of 1.1 mmol (0.075 g) sodium nitrite was added dropwise to an ice-cooled solution of 2 mmol 5-(2,6-dichlorobenzylidene)-4-hydroxy-1,5-dihydropyrrol-2-one (prepared in accordance with H. Poschenrieder et al (Arch. Pharm. Pharm. Med. Chem. 1998, 331, 389–394) and H.-D. Stachel et al (J. Heterocycl. Chem. 1980, vol. 17, pp. 1195–1199 and Liebigs Ann. Chem. 1985, pp. 1692–1696)) in 5 ml glacial acetic acid, while stirring. The resulting solution was then stirred at room temperature for 30 minutes and concentrated in vacuo. The residue is purified by recrystallization from ethanol. The yield of 5-(2,6-dichlorobenzylidene)-pyrrolidine-2,3,4-trione 3-oxime was 65%, with a melting point of 232° C.

Analysis of this compound by means of $^1$H-NMR spectroscopy gave the following signals:

(d6-DMSO, δ in ppm): 11.12 (s, 0.66 H); 11.08 (s, 0.33 H); 7.50–7.48 (m, 2 H); 7.39–7.35 (m 1 H); 6.27 (s, 0.33 H); 6.22 (s, 0.66 H).

Example 9

5-(3-Chlorobenzylidene)-pyrrolidine-2,3,4-trione 3-oxime

An aqueous solution of 1.1 mmol (0.075 g) sodium nitrite was added dropwise to an ice-cooled solution of 2 mmol 5-(3-chlorobenzylidene)-4-hydroxy-1,5-dihydropyrrol-2-one (prepared in accordance with H. Poschenrieder et al (Arch. Pharm. Pharm. Med. Chem. 1998, 331, 389–394) and H.-D. Stachel et al (J. Heterocycl. Chem. 1980, vol. 17, pp. 1195–1199 and Liebigs Ann. Chem. 1985, pp. 1692–1696)) in 5 ml glacial acetic acid, while stirring. The resulting solution was then stirred at room temperature for 30 minutes and concentrated in vacuo. The residue is purified by recrystallization from ethanol. The yield of 5-(3-chlorobenzylidene)-pyrrolidine-2,3,4-trione 3-oxime was 50%, with a melting point of 185° C.

Analysis of this compound by means of $^1$H-NMR spectroscopy gave the following signals:

(d6-DMSO, δ in ppm): 14.69 (s, 0.66 H); 14.53 (s, 0.33 H); 11.47 (s, 0.66 H), 11.40 (s, 0.33 H); 7.72–7.20 (m, 4 H); 6.38 (s, 0.33 H); 6.33 (s, 0.66 H).

Pharmacological Studies a) Studies of the Receptor Binding

The studies to determine the affinity of the compounds according to the invention according to example 1 and 2 for the glycine binding site of the NMDA receptor channel were carried out as described above.

The affinity of the glycine binding site of the NMDA receptor channel was calculated as the $IC_{50}$ (concentration with 50% displacement of the radioactive ligand from its specific binding) by the law of mass action by means of non-linear regression and is stated in the following table 1 as the Ki value after conversion (by the Cheng-Prussoff equation (Y. Cheng, W. H. Prusoff, 1973, Biochem. Pharmacol., vol. 22, pp. 3099–3108)).

TABLE 1

| Example | Glycine binding site of the NMDA receptor channel Ki (μmol/l) |
| --- | --- |
| 1 | 0.116 |
| 2 | 0.430 | b) NMDA/glycine-induced Ion Currents on RNA-injected Xenopus Oocytes.

The study to determine function changes in the NMDA receptor channel due to the compound according to the invention according to example 1 was carried out as described above.

The result of the study of the effect of the compound according to the invention according to example 1 on ion currents induced by NMDA/glycine on RNA-injected oocytes is shown in the following table 2.

TABLE 2

| Example no. | NMDA | NMDA-induced Ion currents (relative current amplitudes) | |
| --- | --- | --- | --- |
| | | NMDA + glycine (0.3 μM) | NMDA + glycine (10 μM) |
| Control | 1.42% | 70.23% | 100% |
| Example 1 | −0.58% | 0.08% | 59.93% |

The studies show the antagonistic action of the compound according to example 1.

c) Formalin Test in Mice

The studies to determine the antinociceptive action of the compounds according to the invention were carried out as described above.

The corresponding results in the formalin test in mice are summarized in the following table 3.

TABLE 3

| Example | % change from the control at 10 mg/kg |
| --- | --- |
| 1 | 63.9 |
| 2 | 36.3 |
| 3 | 47.6 | d) Writing Test in Mice

The study of the analgesic activity was carried out in the phenylquinone-induced writhing in mice as described above. All the compounds according to the invention investigated showed a pronounced analgesic action. The results are summarized in the following table 4.

TABLE 4

| Example | % inhibition of the writhing reaction at 10 mg/kg intravenously |
| --- | --- |
| 3 | 25 |
| 4 | 55 |
| 5 | 50 |
| 6 | 52 |
| 7 | 46 |
| 8 | 51 |
| 9 | 81 |

The forgoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

We claim:

1. A substituted pyrrolidine-2,3,4-trione compound of formula I

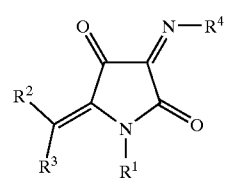

wherein
  $R^1$ represents H, $OR^8$, $COR^5$, $CSR^5$, $NR^6R^7$, $COOR^5$, $CONR^6R^7$, $CSNR^6R^7$, a $C_{1-10}$-alkyl group or an unsubstituted phenyl group,
  $R^2$, $R^3$, which are identical or different, represent H, F, Cl, Br, $CF_3$, $OR^8$, $SR^8$, a $C_{1-10}$-alkyl, an aryl or a heteroaryl group or represent an aryl group bonded via a $C_{1-6}$-alkylene group,
  $R^4$ represents H, OH, $OR^8$, $SR^8$, $COR^5$, $COOR^5$, $COCOR^5$, $CONR^6R^7$, $CSNR^6R^7$ or a $C_{1-10}$-alkyl group,
  $R^5$ represents H or a $C_{1-10}$-alkyl group,
  $R^6$, $R^7$, which are identical or different, represent H, $OR^8$, $COR^5$, $COOR^5$ or a $C_{1-10}$-alkyl group, and $R^8$ represents a $C_{1-10}$-alkyl group, in the form of their racemates, enantiomers, diastereomers or a corresponding physiologically tolerated salt.

2. A substituted pyrrolidine-2,3,4-trione compound according to claim 1, wherein $R^1$ represents a $C_{1-6}$-alkyl group.

3. A substituted pyrrolidine-2,3,4-trione compound according to claim 1, wherein $R^2$ or $R^3$ represents, or $R^2$ and $R^3$ both represent a $C_{1-6}$-alkyl group.

4. A substituted pyrrolidine-2,3,4-trione compound according to claim 1, wherein $R^2$ or $R^3$ represents, or $R^2$ and $R^3$ both represent an aryl group bonded via a $C_{1-3}$-alkylene group.

5. A substituted pyrrolidine-2,3,4-trione compound according to claim 1, wherein $R^4$ represents OH.

6. A substituted pyrrolidine-2,3,4-trione compound according to claim 1, wherein $R^4$ represents $OR^8$.

7. A substituted pyrrolidine-2,3,4-trione compound according to claim 1, wherein $R^4$ represents a $C_{1-6}$-alkyl group.

8. A substituted pyrrolidine-2,3,4-trione compound according to claim 1, wherein $R^5$ represents a $C_{1-6}$-alkyl group.

9. A substituted pyrrolidine-2,3,4-trione compound according to claim 1, wherein $R^6$, or $R^7$ represents, or $R^6$ and $R^7$ both represent, a $C_{1-6}$-alkyl group.

10. A substituted pyrrolidine-2,3,4-trione compound according to claim 1, wherein $R^8$ represents a $C_{1-6}$-alkyl group.

11. A substituted pyrrolidine-2,3,4-trione compound according to claim 1, selected from the group consisting of:

5-(methoxyphenylmethylene)-pyrrolidine-2,3,4-trione 3-oxime;

5-(bromophenylmethylene)-pyrrolidine-2,3,4-trione 3-oxime;

5-benzylidene-pyrrolidine-2,3,4-trione 3-oxime;

5-(2-chlorobenzylidene)-pyrrolidine-2,3,4-trione 3-oxime;

5-(4-chlorobenzylidene)-pyrrolidine-2,3,4-trione 3-oxime;

5-(2,3-dichlorobenzylidene)-pyrrolidine-2,3,4-trione 3-oxime;

5-(2,4-dichlorobenzylidene)-pyrrolidine-2,3,4-trione 3-oxime;

5-(2,6-dichlorobenzylidene)-pyrrolidine-2,3,4-trione 3-oxime; and 5-(3-chlorobenzylidene)-pyrrolidine-2,3,4-trione 3-oxime.

12. A method for the preparation of a substituted pyrrolidine-2,3,4-trione compound of formula I,

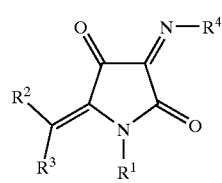

wherein $R^1$ represents H, $OR^8$, $COR^5$, $CSR^5$, $NR^6R^7$, $CONR^5$, $CONR^6R^7$, $CSNR^6R^7$, a $C_{1-10}$-alkyl group or an unsubstituted phenyl group, $R^2$, $R^3$, which are identical or different, represent H, F, Cl, Br, $CF_3$, $OR^8$, $SR^8$, a $C_{1-10}$-alkyl, an aryl or a heteroaryl group or represent an aryl group bonded via a $C_{1-6}$-alkylene group, $R^4$ represents H, $R^5$ represents H or a $C_{1-10}$-alkyl group, $R^6$, $R^7$, which are identical or different, represent H, $OR^8$, $COR^5$, $COOR^5$ or a $C_{1-10}$-alkyl group, and $R^8$ represents a $C_{1-10}$-alkyl group, the method comprising reacting a tetramic acid of formula II

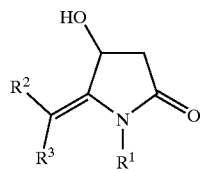

wherein $R^1$ to $R^3$ have the meaning according to formula I, with an aqueous solution of sodium nitrite in an ice-cooled solution.

13. A method for the preparation of a substituted pyrrolidine-2,3,4-trione compound of formula I,

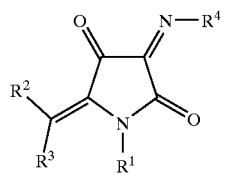

wherein $R^1$ represents H, $OR^8$, $COR^5$, $CSR^5$, $NR^6R^7$, $COOR^5$, $CONR^6R^7$, $CSNR^6R^7$, a $C_{1-10}$-alkyl group or an unsubstituted phenyl group, $R^2$, $R^3$, which are identical or different, represent H, F, Cl, Br, $CF_3$, $OR^8$, $SR^8$, a $C_{1-10}$-alkyl, an aryl or a heteroaryl group or represent an aryl group bonded via a $C_{1-6}$-alkylene group, $R^4$ represents $OR^8$, $R^5$ represents H or a $C_{1-10}$-alkyl group, $R^6$, $R^7$, which are identical or different, represent H, $OR^8$, $COR^5$, $COOR^5$ or a $C_{1-10}$-alkyl group, and $R^8$ represents a $C_{1-10}$-alkyl group, the method comprising reacting a compound of formula I wherein $R^4$ represents OH, with a $C_{1-10}$-alkyl halide in absolute solvents at low temperatures in the presence of strong bases to give rise to a compound of formula I wherein $R^4$ represents $OR^8$.

14. A method for the preparation of a substituted pyrrolidine-2,3,4-trione compound of the formula I,

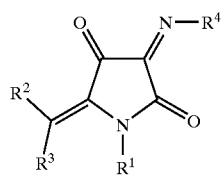

wherein $R^1$ represents H, $OR^8$, $COR^5$, $CSR^5$, $NR^6R^7$, $COOR^5$, $CONR^6R^7$, $CSNR^6R^7$, a $C_{1-10}$-alkyl group or an unsubstituted phenyl group, $R^2$, $R^3$, which are identical or different, represent H, F, Cl, Br, $CF_3$, $OR^8$, $SR^8$, a $C_{1-10}$-alkyl, an aryl or a heteroaryl group or represent an aryl group bonded via a $C_{1-6}$-alkylene group, $R^4$ represents $COR^5$ or $COOR^5$, $R^5$ represents H or a $C_{1-10}$-alkyl group, $R^6$, $R^7$, which are identical or different, represent H, $OR^8$, $COR^5$, $COOR^5$ or a $C_{1-10}$-alkyl group, and $R^8$ represents a $C_{1-10}$-alkyl group, the method comprising reacting a compound of formula I wherein $R^4$ represents $OR^8$, with an acid chloride of the formula $R^5$—(C=O)—Cl or an acid bromide of the formula $R^5$—(C=O)—Br or a chloroformic acid ester of the formula Cl—(C=O)—O—$R^5$ or a fluoroformic acid ester of the formula F—(C=O)—O—$R^5$, or with an open-chain carbonate of the formula $R^5$—O—(C=O)—O—$R^5$, or with a correspondingly substituted cyclic carbonate, wherein in each case $R^5$ represents H or a $C_{1-10}$-alkyl group, in an absolute solvent to give rise to a compound of formula I wherein $R^4$ represents $COR^5$ or $COOR^5$.

15. A method for the preparation of a substituted pyrrolidine-2,3,4-trione compound of formula I

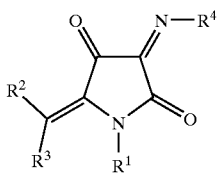

I wherein $R^1$ represents H, $OR^8$, $COR^5$, $CSR^5$, $NR^6R^7$, $COOR^5$, $CONR^6R^7$, $CSNR^6R^7$, a $C_{1-10}$-alkyl group or an unsubstituted phenyl group, $R^2$, $R^3$, which are identical or different, represent H, F, Cl, Br, $CF_3$, $OR^8$, $SR^8$, a $C_{1-10}$-alkyl, an aryl or a heteroaryl group or represent an aryl group bonded via a $C_{1-6}$-alkylene group, $R^4$ represents $CONR^6R^7$ or $CSNR^6R^7$, $R^5$ represents H or a $C_{1-10}$-alkyl group, $R^6$, $R^7$, which are identical or different, represent H, $OR^8$, $COR^5$, $COOR^5$ or a $C_{1-10}$-alkyl group, and $R^8$ represents a $C_{1-10}$-alkyl group, the method comprising reacting a compound of formula I wherein $R^4$ represents OH with aliphatic isocyanates or isothiocyanates at low temperatures in aprotic polar solvents to give rise to a compound of formula I wherein $R^4$ represents $CONR^6R^7$ or $CSNR^6R^7$, and $R^6$ or $R^7$ denotes H.

16. A method according to claim 12, wherein the tetramic acid of formula II is reacted with an aqueous solution of sodium nitrite in an ice-cooled solution of glacial acetic acid.

17. A method according to claim 12, further comprising purifying the compound of formula I wherein $R^4$ represents OH by recrystallization.

18. A method according to claim 17, wherein the purifying is by recrystallization from ethanol.

19. A method according to claim 13, wherein the compound of formula I wherein $R^4$ represents OH is reacted under an inert gas atmosphere.

20. A method according to claim 13, wherein the compound of formula I wherein $R^4$ represents OH is reacted in open-chain or cyclic ethers, or both.

21. A method according to claim 13, wherein the compound of formula I wherein $R^4$ represents OH is reacted in the presence of one or more of alkali metal hydroxides, alkaline earth metal hydroxides and organometallic bases.

22. A method according to claim 13, wherein the compound of formula I wherein $R^4$ represents OH is reacted with $C_{1-6}$-alkyl halides.

23. A method according to claim 14, wherein the compound of formula I wherein $R^4$ represents $OR^8$ is reacted under an inert gas atmosphere.

24. A method according to claim 14, wherein the compound of formula I wherein $R^4$ represents $OR^8$ is reacted in open-chain or cyclic ethers, or both.

25. A method according to claim 14, wherein the cyclic carbonate employed contains 5 or 6 atoms in the ring.

26. A pharmaceutical composition comprising a substituted pyrrolidine-2,3,4-trione compound according to claim 1, or a corresponding pharmaceutically acceptable salt thereof, and a pharmaceutically acceptable excipient.

27. A method for treatment of one or more of pain, inflammatory reactions, allergic reactions, gastritis, diarrhoea, urinary incontinence, cardiovascular diseases, respiratory tract diseases, coughing, epilepsy, schizophrenia, Huntington's disease, Parkinson's disease, cerebral ischaemias, cerebral infarctions, psychoses caused by increased amino acid levels, apoplexies, cerebral oedemas, hypoxia, anoxia, encephalomyelitis, Tourette's syndrome, and perinatal asphyxia comprising administering to a patient in need thereof an effective amount of the pharmaceutical composition of claim 26.

28. A method according to claim 27, wherein the method is for the treatment of one or more of pain, inflammatory reactions, allergic reactions, gastritis, diarrhoea, urinary incontinence, cardiovascular diseases, respiratory tract diseases, coughing and epilepsy.

29. A method according to claim 27, wherein the method is for treatment or prophylaxis of schizophrenia, Huntington's disease, Parkinson's disease, cerebral ischaemias, cerebral infarctions, psychoses caused by increased amino acid levels, apoplexies, cerebral oedemas, hypoxia, anoxia, encephalomyelitis, Tourette's syndrome, or perinatal asphyxia comprising administering the pharmaceutical composition of claim 25 to a patient in need thereof.

* * * * *